(12) United States Patent
Kuehnel et al.

(10) Patent No.: US 10,401,266 B2
(45) Date of Patent: Sep. 3, 2019

(54) EMBEDDING MEDIUM FOR BIOLOGICAL SAMPLES, METHOD FOR PRODUCING EMBEDDED BIOLOGICAL SAMPLES, AND USE THEREOF

(71) Applicants: Medizinische Hochschule Hannover, Hannover (DE); Laser Zentrum Hannover e.V., Hannover (DE)

(72) Inventors: Mark Kuehnel, Hannover (DE); Manuela Kellner, Hannover (DE); Danny Jonigk, Isernhagen (DE); Nicole Izykowski, Hannover (DE); Heiko Meyer, Isernhagen (DE); Raoul-Amadeus Lorbeer, Hannover (DE); Marko Heidrich, Hannover (DE)

(73) Assignee: Laser Zentrum Hannover e.V., Hannover (DE)

( * ) Notice: Subject to any disclaimer, the term of this patent is extended or adjusted under 35 U.S.C. 154(b) by 112 days.

(21) Appl. No.: 15/319,611

(22) PCT Filed: Jun. 19, 2015

(86) PCT No.: PCT/EP2015/063808
§ 371 (c)(1),
(2) Date: Dec. 16, 2016

(87) PCT Pub. No.: WO2015/193469
PCT Pub. Date: Dec. 23, 2015

(65) Prior Publication Data
US 2017/0212020 A1 Jul. 27, 2017

(30) Foreign Application Priority Data
Jun. 19, 2014 (DE) .................. 10 2014 108 642

(51) Int. Cl.
*G01N 1/36* (2006.01)
*G01N 1/28* (2006.01)
(Continued)

(52) U.S. Cl.
CPC .............. *G01N 1/36* (2013.01); *C12Q 1/68* (2013.01); *G01N 1/286* (2013.01); *G01N 1/30* (2013.01);
(Continued)

(58) Field of Classification Search
None
See application file for complete search history.

(56) References Cited

U.S. PATENT DOCUMENTS 6,266,109 B1 * 7/2001 Yamaguchi ........... G02F 1/1334
349/86
6,291,180 B1 * 9/2001 Chu ......................... G01N 1/30
422/20

(Continued)

FOREIGN PATENT DOCUMENTS

DE           40 32 300 A1     4/1992
DE    10 2012 210 185 A1    12/2003

(Continued)

OTHER PUBLICATIONS

"Norland Optical Adhesive 68" from norlandprod.com [retrieved on Sep. 26, 2018]. Retrieved from the Internet: <URL: www.norlandprod.com/adhesives/noa%2068.html>.*

(Continued)

*Primary Examiner* — Robert T. Crow
(74) *Attorney, Agent, or Firm* — W & C IP

(57) ABSTRACT

In a first aspect, the invention relates to the use of a UV-polymerizable composition as an embedding medium for biological samples. The UV-polymerizable composition is a composition with a refractive index ranging from n=1.45

(Continued)

to n=1.6 after a polymerization process. In another aspect, the invention relates to a method for producing embedded biological samples using said UV-polymerizable composition and to the embedded biological samples themselves. The biological samples can be used in a wide variety of areas, such as diagnostics among others, and are suitable in particular for RNA-based diagnostics.

16 Claims, 3 Drawing Sheets

(51) Int. Cl.
  *G01N 1/30* (2006.01)
  *C12Q 1/68* (2018.01)
  *G01N 1/44* (2006.01)
  *G06K 9/00* (2006.01)

(52) U.S. Cl.
  CPC ....... *G01N 1/44* (2013.01); *G01N 2001/2886* (2013.01); *G01N 2001/305* (2013.01); *G01N 2001/364* (2013.01); *G06K 9/0014* (2013.01); *G06K 9/00134* (2013.01)

(56) References Cited

U.S. PATENT DOCUMENTS

| | | | | |
|---|---|---|---|---|
| 2009/0131543 | A1* | 5/2009 | Weitz | A61K 9/113 |
| | | | | 516/54 |
| 2011/0052446 | A1* | 3/2011 | Hirano | G01N 35/00069 |
| | | | | 422/68.1 |
| 2011/0300131 | A1* | 12/2011 | Ryan | C07K 16/2875 |
| | | | | 424/133.1 |
| 2014/0072720 | A1* | 3/2014 | Watkins | H01L 51/0015 |
| | | | | 427/487 |

FOREIGN PATENT DOCUMENTS

| | | |
|---|---|---|
| DE | 10 2010 013950 A1 | 10/2011 |
| EP | 0 103 477 A2 | 3/1984 |
| EP | 0 136 014 A2 | 4/1985 |
| WO | 00/16065 A1 | 3/2000 |

OTHER PUBLICATIONS

Hobot et al.; "Periplasmic Gel: New Concept Resulting from the Reinvestigation of Bacterial Cell Envelope Ultrastructure by New Methods"; Journal of Bacteriology, vol. 160, No. 1, Oct. 1984, pp. 143-152.

Kellner et al.; "Imaging of the mouse lung with scanning laser optical tomography (SLOT)"; Journal of Applied Physiology, vol. 113, 2012, pp. 975-983.

Chung et al.; "Structural and molecular interrogation of intact biological systems"; Nature, vol. 497, May 16, 2013, pp. 332-339.

* cited by examiner

EMBEDDING MEDIUM FOR BIOLOGICAL SAMPLES, METHOD FOR PRODUCING EMBEDDED BIOLOGICAL SAMPLES, AND USE THEREOF

In a first aspect, the invention is directed to the use of a UV-polymerizable composition as embedding medium for biological samples. Said UV-polymerizable composition is a composition having a refractive index after polymerization in the range from n=1.45 to n=1.6. In a further aspect, the application is directed to a method for producing embedded biological samples using said UV-polymerizable composition, and also toward these embedded biological samples themselves. These biological samples are usable in the most varied fields, inter alia diagnostics, and are also suitable, in particular, for RNA-based diagnostics. Therefore, a further aspect is directed to a method for examining biological samples that comprises an imaging method, a histological method and optionally a molecular-biological method of the same sample with spatial correlation.

PRIOR ART

In the case of light-microscopic imaging methods such as optical projection tomography (OPT), scanning laser optical tomography (SLOT), light sheet fluorescence microscopy (SPIM) or ultramicroscopy (UM), in which the fixed sample is moved in a controlled manner in the light (usually laser light), frequently unwanted movements of the sample or within the sample occur, as a result of which reconstruction of the data sets is made more difficult. Movement artifacts occur and/or the assignment of the individual image planes to one another (e.g. in SPIM) is made more difficult.

Precisely in the case of biological samples, it is in addition desirable that firstly an examination proceeds via imaging methods such as the abovementioned, and secondly diagnostic examinations of the sample are carried out, e.g. histological examinations or examinations and diagnostics on sample sections including examinations at the nucleic acid level. To date, samples for histopathological assessment are embedded, sectioned, histologically stained and then assessed. Sometimes these sections are additionally examined by means of laser microdissection with subsequent isolation of components, including RNA isolation and RNA diagnostics. In such examinations, however, frequently the spatial correlation is lost, since only a two-dimensional inspection of the sections can proceed, and for the three-dimensional depiction a multiplicity of consecutive sections would have to be analyzed. Adjacent levels remain hidden in the case of such a histopathological assessment. Furthermore, assessment of a sample on the basis of sections is only possible in a random-sample manner and includes the risk of possibly overlooking important particularities, e.g. a beginning metastasis.

Such impairments can be overcome by three-dimensional imaging methods such as the abovementioned OPT, SLOT, SPIM, ultramicroscopy (including multiphoton microscopy and scanning confocal microscopy). For such an examination using the abovementioned imaging methods, however, it is necessary that the sample is embedded in a transparent manner that as far as possible does not affect the imaging method. Such an adaptation means, in particular, that the refractive indices of the sample and the embedding medium match as far as possible, in such a manner that the light is scattered as little as possible during the transillumination.

Optimized embedding media are known that permit an optical examination with three-dimensional imaging methods. Said media are adapted in their refractive index to the sample under examination, in order to eliminate refraction artifacts in such a manner that electromagnetic waves, such as light (visible and non-visible light) can be carried out as far as possible unaffected. Such embedding media are also termed clearing media.

A disadvantage of said clearing media is that they are solely present in the liquid state. As a liquid having clearing action, i.e. being suitable for three-dimensional imaging methods, materials such as methyl salicylate/benzyl benzoate (MS/BB), benzyl benzoate/benzyl alcohol (BABB), glycerol, Scale and xylene are described.

Although these liquid clearing media permit the adaptation of the refractive index of said media to refractive indices necessary for the light and permit an optimized light yield for corresponding examinations (i.e. a "clearing of the sample"), a permanent immobilization of the sample under examination, i.e. a permanence and stainability and also sectionability is not provided, however. As a result, laser tomographic approaches such as OPT and SLOT, with samples that are then to be subjected to further histopathological examinations, can only be carried out with restrictions or not at all.

Primarily in the field of histology, there are extensive studies on possible embedding methods and embedding media. Thus, inter alia, synthetic resins optimized in respect to sectionability, permanence and stainability are used for histology, but the aspect of the transparency, that is to say suppression of light scattering within the sample, has to date been neglected. That means that adapting the embedding medium to the sample in order to permit an optical clearing of the sample has not been taken into account to date. Embedding media predominantly used to date for histology using corresponding carbons are selected in such a manner that they are suitable for two-dimensional examinations of thin sections, but not for three-dimensional examinations of tissue samples. These synthetic resins do not permit provision of clear, i.e. see-through embedding media. That is to say although the media are transparent to the extent that they permit transmitted-light or fluorescence microscopy, they are, however, not geared to suppressing scattering of the light by the media. However, this is precisely what is of importance in the abovementioned three-dimensional imaging methods.

These systems used in histopathology are usually based on chemically-initiated polymerized plastics. For this purpose there are various plastics, customarily based on epoxides, acrylics or acrylates or methacrylates. Usually, in addition, a thermal polymerization of the medium is necessary. Such a polymerization via supply of heat, however, is harmful for the structure under examination itself. In particular, sensitive molecules, e.g. nucleic acid molecules such as RNA molecules, are destroyed by this supply of heat.

An important problem, in addition, is that the starters necessary for polymerization of the monomers must be added to the medium before embedding and infusion, and that these starters then already to a certain extent initiate the polymerization and thus make the infusion difficult. Correspondingly, the desired quality of embedding, without air bubbles, streaks etc. cannot be achieved.

Kellner M. et al., J. Appl Physiol, 2012, 113, 975-983 describes the depiction of a mouse lung by means of SLOT using MS/BB. For the subsequent histology, changing the embedding of the sample from the liquid MS/BB into a synthetic resin, here Technovit 8100, with a plurality of substitution steps, is necessary.

To solve the problem of embedding a biological sample with simultaneous clearing, a method termed "clarity" was described by Chung K. et al., Nature, 2013, 497, 332. This method is based on the use of acrylamide and bisacrylamide and also formaldehyde carbons, that are first infused and then hybridized in heat. This is followed by an electrophoretic method in order to achieve clearing of the immobilized sample. The samples thus produced, however, as hydrogels, have a tendency to be too soft for further processing, in particular sectioning. Long-term storage or preparation for subsequent histology is, in addition, not possible with this method without additional operating steps.

DE 10 2012 210 185 discloses a UV-curable embedding medium for light and fluorescence microscopy. UV-curable media have the advantage that the sample is cured by UV-light irradiation, and therefore heating and thus possible destruction of molecules in the sample are prevented. The UV-polymerizable composition described there is a composition based on a polymerizable organic compound and an alkoxysilane having a polymerizable group. In this case it is described that, using said materials, the setting of the refractive index can be adapted with respect to the purpose of use.

It is an object of the present invention to provide novel embedding media suitable for infusion of samples, which embedding media permit sample clearing for not only three-dimensional imaging methods but also for a molecular profiling, e.g. of correspondingly produced histological sections, on one and the same sample. That is to say the invention is directed to an embedding medium that is suitable not only for said imaging methods, but is also suitable for histological examinations on the same sample, including good sectionability and good storability of the sample, and also molecular-biological examinations thereof also at a later timepoint.

According to the invention, this object is achieved by using a UV-polymerizable composition as embedding medium for biological samples. These UV-polymerizable compositions permit the provision of embedded biological samples using a sectionable plastic that permits the preparation of histological to electron-microscopic section preparations, and at the same time permits an RNA extraction from the embedded samples. In advance, 3D imaging methods, such as 3D tomography examinations, e.g. laser tomography methods can be used for examining the sample in order to obtain 3D models of the sample.

According to the invention, it is therefore possible, using the described UV-polymerizable composition, not only to generate 3D models of the sample, but also subsequently to permit diagnostic methods including examinations of RNA expression.

The samples exhibit in this case an outstanding storage stability and permanence, and also good sectionability and are distinguished, in particular, by refractive indexes such that permit a three-dimensional imaging method of the sample. Such three-dimensional imaging methods are, in particular, the said tomographic methods including OPT, SLOT, SPIM and ultramicroscopy. The UV-polymerizable compositions according to the invention lead to clearing media that permit an infusion and subsequent embedding of the three-dimensional biological samples.

In the present case, the expression "embedding medium" is taken to mean a medium which is completely infused into the biological sample, and into which the biological sample is embedded, in such a manner that said biological sample is protected against external effects. Such an embedding medium in the present case is also termed a "clearing medium". This clearing medium is a medium that, together with the sample, appears clear, that is to say transparent, and therefore the embedding medium allows irradiation of the sample with electromagnetic radiation, in particular visible and/or non-visible light, and in this case causes a lowest possible scattering of the light. According to the invention, said UV-polymerizable composition therefore has a refractive index which substantially accords with the refractive index of the sample.

According to the invention, therefore, the refractive index of the UV-polymerizable composition after polymerization is in the range from $n=1.45$ to $n=1.6$. Preferably, this range is in a range from $n=1.550$ to $n=1.565$. In an embodiment, the refractive index in this case is in a range from 1.552 to 1.559.

It has been found that, for a multiplicity of biological samples, such a refractive index is suitable to use said biological sample not only in imaging three-dimensional methods such as the said light-microscopic imaging methods, but in addition the medium according to the invention permits good durability and storability in order to permit, at a later timepoint, sections and therefore two-dimensional examinations including diagnostic examinations of molecules present in the sample, such as nucleic acid fragments, including an RNA extraction.

The present use permits the correlative application of different analytical methods with a single sample by clearing the sample in a sectionable plastic which permits the preparation of histological to electron-microscopic section preparations and at the same time permits RNA extraction from the embedded samples. Therefore, successively, by laser tomographic methods, models of the samples can be generated and then histopathological examinations including determination of the RNA expression pattern of the sample can be carried out. These examinations can, on account of the good storage stability of the sample, be carried out at different times.

"Correlative application" or "correlation", as the expression is used herein, means that the data from the three-dimensional imaging method can be related to the data obtained in the histological and optionally molecular-biological methods. It is possible thereby to project the information from the histological and optionally molecular-biological method into the three-dimensional image.

In an embodiment, the UV-polymerizable composition comprises a mercapto ester compound. Mercapto esters comprise the group R1-(C=O)—S—R2 and are also called thioesters or thiol esters. In this case, the radicals R1 and R2 are organyl groups, e.g. acrylic groups or aryl groups. The mercapto esters can possibly also be thionoesters, i.e. compounds having the group R1-(C=S—O)—R2. Suitable mercapto ester compounds are known to those skilled in the art. In an embodiment, said mercapto ester compound or mixture of different mercapto ester compounds is present in the composition with a fraction of at least 40% by weight. The fraction of the mercapto ester compound can be in this case in a range from 40 to 70% by weight, such as 45 to 65% by weight. In a further embodiment, the mercapto ester fractions of a mercapto ester compound or a mixture of mercapto ester compounds can be present in an amount from 40 to 85% by weight, such as 50 to 80% by weight, e.g. 55 to 75% by weight. In this case, a first mercapto ester compound can be present with a fraction of from 40 to 60% by weight, while the second mercapto ester compound is present with a fraction of 15 to 35% by weight. These two mercapto ester compounds are added in this case in their fractions in such a manner that the total fraction of the mercapto ester compounds is in the abovementioned range, e.g. in the range from 50 to 80% by weight, such as 55 to 75% by weight.

In a further embodiment, the UV-polymerizable compound additionally comprises a polymerizable acrylate and/or methacrylate compound. In this compound, the fraction of the mercapto ester compound can be in a range from e.g. 40 to 70% by weight, while the fraction of the acrylate and/or methacrylate compounds are in the range from 50 to 25% by weight, the total fraction of mercapto ester compounds and acrylate and/or methacrylate compounds in this case is in the range from 45 to 80% by weight, such as 50 to 75% by weight, e.g. 60 to 70% by weight.

Suitable mercapto ester compounds and suitable acrylate and/or methacrylate compounds are known to those skilled in the art. Suitable acrylate and/or methacrylate compounds comprises tetrahydrofurfuryl methacrylate.

In an embodiment, the UV-polymerizable composition in this case is a composition which, before polymerization, has a refractive index in the range from n=1.45 to 1.6, such as n=1.50 to 1.55.

Where not stated otherwise, the expression "comprising" or "including" or "containing" comprises embodiments of "consisting of".

Where not specified otherwise, the indefinite article "a" and the definite article "the" comprise not only one but also a plurality of said named items.

The biological sample is, in particular, a three-dimensional biological sample, wherein the smallest edge length of said biological sample is at least 50 µm, such as at least 100 µm.

In an embodiment, the biological sample is a biological sample from an animal, in particular from a human.

It has been found that the samples embedded by means of the use according to the invention of the UV-polymerizable composition as embedding medium can be used not only in three-dimensional imaging methods in order to be able to represent the three-dimensional structure of the sample, but it also permits a long-term storage of said sample and later further analysis thereof, including a molecular-biological analysis, such as diagnostics, e.g. on a nucleic acid level, such an RNA level. Surprisingly, it has been found that, using the UV-polymerizable composition according to the invention in a sample thus embedded, even after a relatively long storage of some months, e.g. of more than six months, molecular-biological examinations including isolation and determination of the expression profile of RNA. That is to say, from said samples embedded according to the invention, after a period of over six months, the production of RNA profiles and examination of RNA expression patterns was possible.

Using the method according to the invention, therefore, not only can three-dimensional models be prepared from one and the same sample, but also two-dimensional analyses can be carried out subsequently thereto. As a result, a correlation of the results obtained in the two-dimensional steps with the previously prepared three-dimensional model is possible. The corresponding histological and molecular-biological examinations on the section can be depicted in the three-dimensional space.

In a further aspect, the present invention is directed to a method for producing embedded biological samples including embedded three-dimensional biological samples, in particular those where said three-dimensional sample has a smallest edge length of at least 50 µm, such as at least 100 µm. For this purpose, the method according to the invention comprises the steps of dewatering the biological sample, infusing a UV-polymerizable composition, in particular a UV-polymerizable composition as defined in the present case, into the biological sample and curing thereof using the biological sample infused with the UV-polymerizable composition with light having a wavelength of ≤470 nm.

Suitable methods for dewatering biological samples are known to those skilled in the art. Such a dewatering can be carried out, e.g., by means of an ascending alcohol series, such as an ascending ethanol series. Alternatively thereto, an ascending DMSO series can proceed. Optionally, subsequently thereto, dewatering by means of xylene can be carried out.

The step of fixing the biological sample can precede dewatering the biological sample. Such a fixing comprises, e.g., a fixing with aldehyde mixtures or alcohols. The suitable fixing methods, as are used for biological samples, are known to those skilled in the art. These are in this case general fixing methods as are used in microscopy.

The infusion of the UV-polymerizable composition proceeds, in an embodiment, under reduced pressure. Optionally, the curing can also proceed under reduced pressure. The infusion of the biological sample with the UV-polymerizable composition permits a distribution of this composition in the biological sample, wherein as few as possible contaminants impairing the imaging method are present. In particular, the infusion under reduced pressure permits prevention of the formation of air bubbles or streaks.

Curing the UV-polymerizable composition with radiation having a wavelength of ≤470 nm can proceed continuously or discontinuously. The suitable conditions are known to those skilled in the art or those skilled in the art can determine these simply. These also depend, in particular, on the strength of the radiation source. Optionally, the biological sample can be cooled during the irradiation and curing or/and in the case of discontinuous irradiation, during and/or between the irradiations, in order to prevent damage to tissue and molecules in the biological sample.

In a further aspect, the application is directed to embedded biological samples, in particular embedded three-dimensional biological samples having a smallest edge length of at least 50 µm, such as at least 100 µm, obtainable using a UV-polymerizable composition such as described herein or obtainable according to a method according to the invention. In the case of the embedded biological sample, in particular the embedded three-dimensional biological sample, in one aspect it is a human or animal tissue sample. However, plant or mycological samples etc. can also be examined.

The biological samples embedded according to the invention are advantageous, since they permit the combination of a three-dimensional microscopy, e.g. a tomography, such as SLOT, and subsequent molecular profiling in the context of histopathological analyses.

These biological samples embedded according to the invention are suitable in this case in particular for use in diagnostics, and here in molecular diagnostics. An advantageous embodiment comprises in this case the use of the embedded biological samples in the RNA-based diagnostics. It has surprisingly been found that the embedded biological samples, even after relatively long storage, permit RNA extraction and therefore RNA profiling of the sample. As a result, it is possible to prepare not only a three-dimensional model of the biological sample, but also to permit a molecular profiling, e.g. of the RNA expression.

On account of the transparent properties of the embedding medium, it is still possible, using a suitable method, to detect marker molecules, e.g. dyes, antibodies, etc., present even in the as yet non-sectioned three-dimensional sample.

The use of such embedded biological samples is multifold. As stated, microscopic diagnostics can be extended to the third dimension. Histopathological changes can be assessed in the spatial context. In addition, it is possible to use said samples from the embryonic development research in the field of regeneration medicine and stem cell biology, but also in the diagnostics of tumor diseases and possible metastasis of tissues.

According to the invention, therefore, the most varied tissue types, such as brain, bone and cartilage, e.g. arthritis models, but also lymph nodes in cancers (e.g. for examination of metastasis) but also inflammations and fibroses and also emphysemas can be examined.

The invention finally provides the use of a kit or a system for embedding biological samples comprising the herein-described UV-polymerizable composition, this kit or system comprises in this case UV-polymerizable compositions as a multicomponent, separately present composition, wherein the desired refractive index can be set by suitable mixing of these two components. Alternatively, compositions can be provided, the refractive index of which is set in advance to a value on the basis of the defined fractions of the components.

Finally, the present application is directed to a method for examining a biological sample, wherein said sample is subjected both to an imaging method and subsequently to a histological, and optionally molecular-biological method, comprising the steps:
a) producing embedded biological samples using a method according to the invention;
b) carrying out a three-dimensional imaging method;
c) producing optionally consecutive histological sections of the biological sample that was produced in a) and subjected in b) to a three-dimensional imaging method;
d) histological and optionally molecular-biological examination of the sections obtained in step c).

As already described above, on the basis of the 3D data, appropriate selection of the sectioning planes can proceed, in order to examine objects present there by histology and optionally by molecular biology. That means, firstly a preselection of the sectioning planes can proceed on the basis of the 3D data. Secondly, the object can be examined in randomly selected sections and then these data thus obtained can be projected into the 3D model.

In an embodiment, in this case, the step of correlation of the three-dimensional imaging from step b) with the histological and optionally molecular-biological examinations from step d) additionally takes place. That is to say the data obtained in step b) of the three-dimensional structure of the biological sample can be correlated with the two-dimensional histologically determined data of the same sample. Said histological data can in this case optionally contain molecular-biological data, including RNA profiling.

The imaging method can in this case be a light-microscropic or tomographic method, in particular OPT; SLOT; STIM and ultramicroscopy. In an aspect, in this case the histological method is a method comprising a microdissection of individual regions, for example individual cells. This can proceed, in particular, using a laser microdissection.

The method according to the invention can in this case comprise a molecular-biological method, in particular diagnostics at the nucleic acid level. Such diagnostics at the nucleic acid level can be RNA-based diagnostics, for example RNA-profiling.

The invention is described in more detail with reference to the following examples, without being restricted thereto.

DETAILED DESCRIPTION

Figure 1:
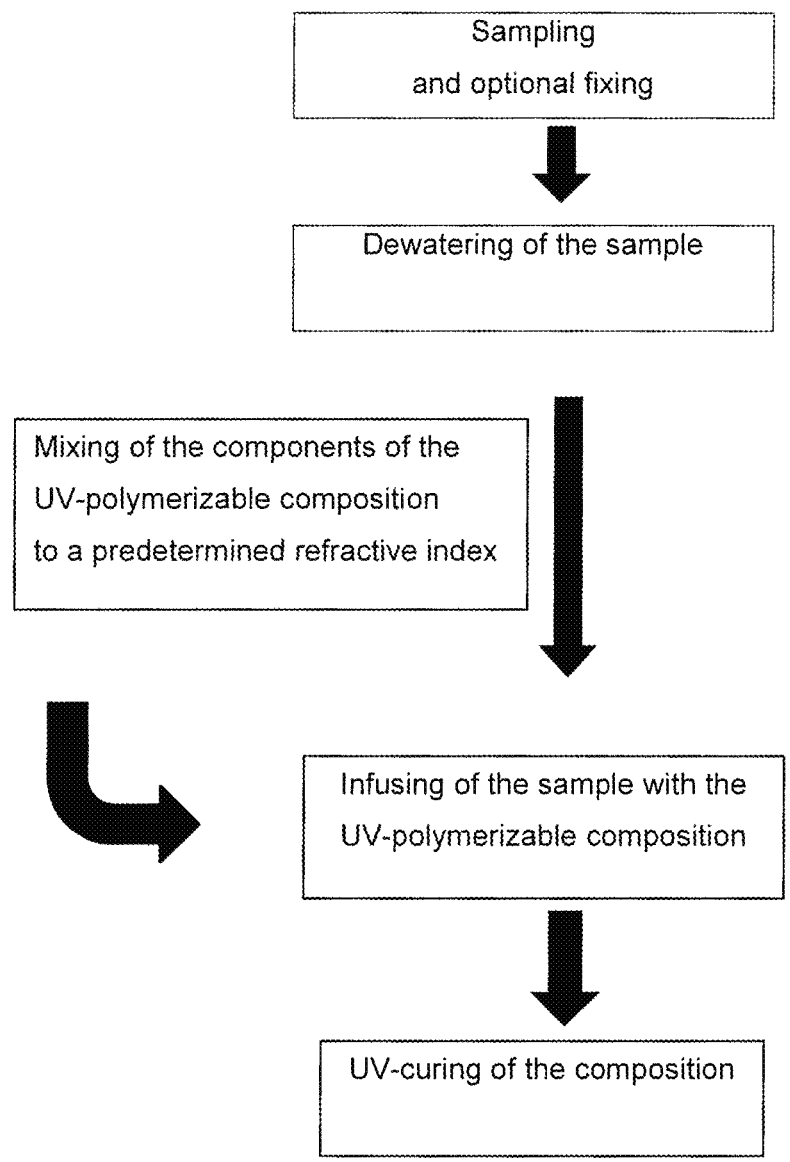
FIG. 1 is a schematic drawing of processing steps according to the invention.

In this case, the processing steps are shown schematically in FIG. 1:

In a first step, the sample is taken and optionally fixed. The sample is then dewatered. Subsequently thereto, the embedding medium according to the invention is infused with the composition according to the invention after said composition has been appropriately produced. Subsequently, there proceeds the polymerization by means of UV irradiation to obtain a biological sample embedded according to the invention.

Figure 3:
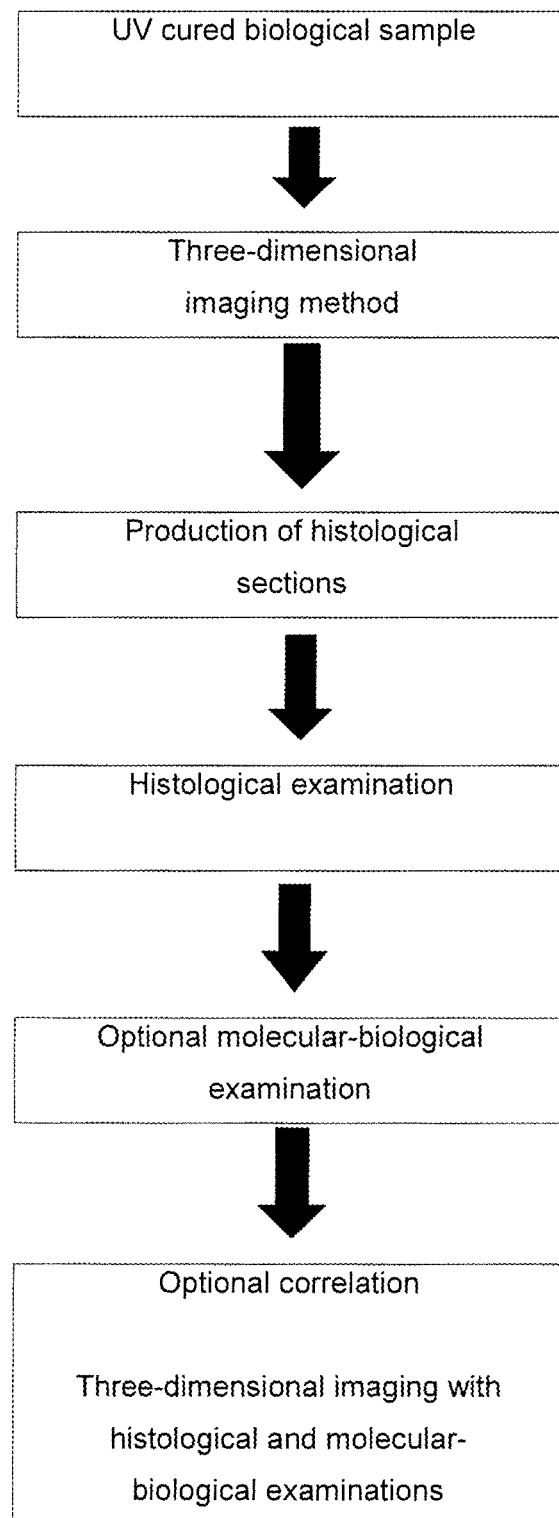
FIG. 3 is a schematic drawing of processing steps for examining biological samples.

In FIG. 3, the processing steps of the method according to the invention for examining biological samples are shown schematically. In this case, the processing steps shown in FIG. 1 are carried out. This is followed by carrying out the imaging method, for example using tomographic methods. In a further step, the production of optionally consecutive histological sections using suitable devices follows thereon.

Subsequently thereto, sections obtained in such a manner are subjected to a histological examination. This histological examination can include a molecular-biological examination.

In an embodiment, correlation of the data of the three-dimensional imaging, that is to say the three-dimensional model, with the histological and optionally molecular-biological data then takes place.

EXAMPLE 1

The sample is taken and washed with known agents, e.g. sodium chloride solution, and then fixed. The fixing proceeds using known media, e.g. aldehyde mixtures, such as 4% of p-formaldehyde or 0.1% glutaraldehyde.

The samples thus fixed are then dewatered in an ascending alcohol series and then transferred to xylene. The steps in this were as follows:
30% ethanol in distilled water, 2-4 hours,
50% ethanol in distilled water, 2-4 hours,
70% ethanol in distilled water, 2-4 hours,
90% ethanol in distilled water, overnight,
99.8% ethanol, 4 hours,
100% ethanol, 4 hours,
50% ethanol/50% xylene, overnight,
100% xylene, 4 hours,
100% xylene, 4 hours.

Subsequently, xylene was mixed with the UV-polymerizable agent in a proportion of 1:1 and the sample was incubated overnight in a vacuum cabinet at <100 mbar with said 1:1 mixture. Then, the biological sample was treated with 100% UV-polymerizable composition for 6 hours in the vacuum cabinet at <100 mbar.

Production of the UV-Polymerizable Sample:

The UV-polymerizable sample was produced from a mixture of NOA (Norland Optical Adhesive 68, Norland Products Inc., Cranbury, USA and Norland Optical Adhesive 71, Norland Products Inc., Cranbury, USA). The mixing ratio of these two components was set in this case in such a manner that the refractive index of said UV-polymerizable composition had a value of approximately 1.523 before polymerization.

A preferred mixing ratio in this case is one of 1:7 of NOA 68:NOA 71.

According to the invention, a 24-hour polymerization takes place as curing of said plastic, which led to a refractive index of approximately 1.556. To measure the refractive index in the polymer, plastic blocks are polymerized parallel to the embedded samples, which blocks are of identical size to the embedded samples themselves. These plastic blocks are then, in preparation for the refractive index measurement on the refractometer (Müller Abbe Refractometer AR-4), are ground flat and finally brought onto the measuring prism with a contact medium of a higher refractive index.

The polymerization can proceed continuously or batchwise.

Batchwise Polymerization:

The sample, for curing, was charged in syringes (fill level 3 to 5 ml, depending on sample size) together with the UV-polymerizable composition and held with an additional sample holder device. For this purpose, polymerization was started in the sample by alternating phases each of 1 minute of UV light (Leica EM AFS2) and 1 minute with cooling at 4° C. After 30 minutes, the syringe was inverted and the additional sample holder device mounted in advance was removed, and so the sample was present positioned in the center of the syringe. Subsequently, in alternating steps of UV and cooling, the polymerization was continued and finally ended by long-term irradiation with UV at room temperature.

Figure 2:
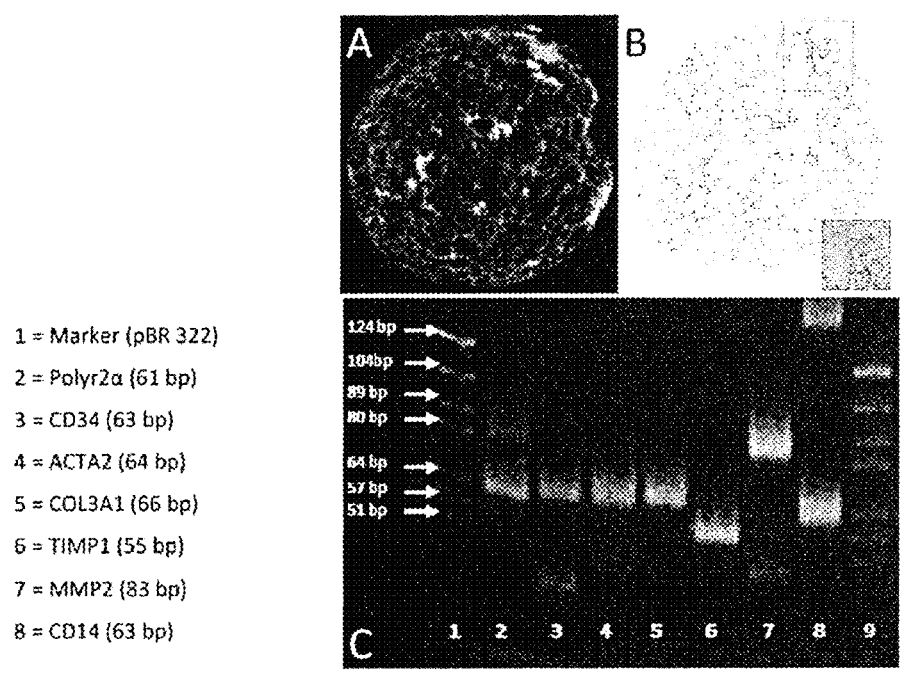
FIG. 2A is an image of a sample studied using SLOT.
FIG. 2B is an image of a sample stained with Hemalaun.
FIG. 2C is an RNA expression profile.

FIG. 2A-C show the detection of RNA from a human lung sample embedded according to the invention. After the embedding of the sample according to the invention, said sample was studied microscopically by means of SLOT (FIG. 2A) and then 4 µm-thick sections were prepared and stained with Hemalaun (FIG. 2B). Areas of interest were cut out (excerpt B) using a laser microdissection system and incubated overnight in proteinase K buffer. Subsequently, the RNA suspended in the supernatant was purified by phenol-chloroform precipitation, and the synthesis of cDNA and amplification with suitable primers proceeded according to known methods. FIG. 2C shows an RNA expression profile having the following markers: Polyr2a (polymerase 2alpha), BMP4 (bone morphogenic protein 4), CD34, ACTA2 (alpha-2 smooth muscle-actin), COL3A1 (collagen 3A1), TIMP1 (metallopeptidase inhibitor 1), MMP2 (matix metalloprotease 2), CD14.

RNA extraction, transcription and amplification of the cDNA proceeded using known methods.

The invention claimed is:

1. A method for producing an embedded biological sample, comprising the steps:
    a) dewatering the biological sample,
    b) infusing a UV-polymerizable composition into the biological sample, wherein said UV-polymerizable composition has a refractive index after polymerization in the range from n=1.45 to n=1.6,
    c) embedding the infused biological sample by curing the UV-polymerizable composition with light having a wavelength of ≤470 nm, and the UV-polymerizable composition comprises a mercapto ester compound.

2. The method as claimed in claim 1, whereby polymerization does not proceed continuously at the start.

3. The method as claimed in claim 1, wherein the biological sample was fixed before the dewatering.

4. The method as claimed in claim 1, wherein at least the infusion of the UV-polymerizable composition is carried out under vacuum.

5. The method as claimed in claim 1, wherein the dewatering of the biological sample proceeds i) by means of an ascending alcohol series or ii) by means of an ascending DMSO series.

6. The method as claimed claim 1, wherein the mercapto ester compound is present in the UV-polymerizable composition at at least 40% by weight.

7. The method as claimed in claim 1, wherein the refractive index of the UV-polymerizable composition before polymerization is in a range from n=1.4 to 1.6.

8. The method as claimed in claim 1, wherein the UV-polymerizable composition additionally comprises at least one of a polymerizable acrylate compound and a methacrylate compound.

9. The method as claimed in claim 1, wherein the biological sample is a three-dimensional biological sample and wherein said three-dimensional sample has a smallest edge length of at least 50 µm.

10. The method according to claim 1 wherein said UV-polymerizable composition has a refractive index after polymerization in the range from n=1.550 to n=1.565.

11. The method according to claim 2 further comprising cooling the biological sample between incidences of light having a wavelength of ≤470 nm.

12. The method as claimed in claim 3 wherein the biological sample was fixed with aldehyde mixtures or alcohols.

13. The method as claimed in claim 5, wherein the dewatering of the biological sample proceeds by means of an ascending ethanol series.

14. The method according to claim 5 further comprising subsequent dewatering in xylene.

15. The method as claimed in claim 7 wherein the refractive index of the UV-polymerizable composition before polymerization is in the range from n=1.50 to 1.55.

16. The method as claimed in claim 9 wherein the biological sample is a three-dimensional biological sample and wherein said three-dimensional sample has a smallest edge length of at least 100 µm.

* * * * *